United States Patent
Lin et al.

(10) Patent No.: US 10,668,120 B2
(45) Date of Patent: *Jun. 2, 2020

(54) ANTIBACTERIAL INDIGO NATURALIS OR INDIGO-PRODUCING PLANT EXTRACT AND USE THEREOF

(71) Applicant: Galderma S.A., Cham (CH)

(72) Inventors: Yin-Ku Lin, Keelung (TW); Philippe Andres, Peymeinade (FR); Laurent Chantalat, Antibes (FR)

(73) Assignee: Galderma SA, Cham (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/564,944

(22) PCT Filed: Apr. 8, 2016

(86) PCT No.: PCT/EP2016/057775
§ 371 (c)(1),
(2) Date: Oct. 6, 2017

(87) PCT Pub. No.: WO2016/162490
PCT Pub. Date: Oct. 13, 2016

(65) Prior Publication Data
US 2018/0110819 A1 Apr. 26, 2018

(30) Foreign Application Priority Data

Apr. 9, 2015 (EP) .................................... 15163069

(51) Int. Cl.
| | | |
|---|---|---|
| *A61K 36/315* | (2006.01) | |
| *A61K 36/19* | (2006.01) | |
| *A61K 36/48* | (2006.01) | |
| *A61P 17/00* | (2006.01) | |
| *A61P 31/04* | (2006.01) | |
| *A61K 8/49* | (2006.01) | |
| *A61K 8/92* | (2006.01) | |
| *A61K 31/404* | (2006.01) | |
| *A61K 36/195* | (2006.01) | |
| *A61K 36/70* | (2006.01) | |
| *A61C 19/00* | (2006.01) | |

(52) U.S. Cl.
CPC ............ *A61K 36/315* (2013.01); *A61C 19/00* (2013.01); *A61K 8/492* (2013.01); *A61K 8/922* (2013.01); *A61K 31/404* (2013.01); *A61K 36/19* (2013.01); *A61K 36/195* (2013.01); *A61K 36/48* (2013.01); *A61K 36/70* (2013.01); *A61P 17/00* (2018.01); *A61P 31/04* (2018.01); *A61K 2236/33* (2013.01); *A61K 2236/39* (2013.01); *A61K 2236/50* (2013.01); *A61K 2236/51* (2013.01); *Y02A 50/473* (2018.01)

(58) Field of Classification Search
None
See application file for complete search history.

(56) References Cited

U.S. PATENT DOCUMENTS

| | | | |
|---|---|---|---|
| 8,784,905 B2 * | 7/2014 | Lin | ...................... A61K 36/315 424/725 |
| 9,833,438 B2 | 12/2017 | Andres et al. | |
| 9,861,673 B2 | 1/2018 | Lin et al. | |
| 10,232,006 B2 | 3/2019 | Chantalat et al. | |
| 10,251,926 B2 | 4/2019 | Lin et al. | |
| 2003/0054047 A1 | 3/2003 | Zhao | |
| 2010/0034757 A1 | 2/2010 | Fujii et al. | |
| 2012/0213868 A1 | 8/2012 | Lin | |
| 2013/0331400 A1 * | 12/2013 | Kusakari | .............. A61Q 17/005 514/257 |
| 2014/0243354 A1 | 8/2014 | Chantalat et al. | |

FOREIGN PATENT DOCUMENTS

| | | |
|---|---|---|
| CN | 1317322 A | 10/2001 |
| CN | 1586506 A | 3/2005 |
| CN | 1316996 C | 5/2007 |
| CN | 102247415 A | 11/2011 |
| CN | 102351863 A | 2/2012 |
| CN | 102641313 A | 8/2012 |
| CN | 103429249 A | 12/2013 |
| CN | 103766415 A | 5/2014 |
| CN | 103992260 A | 8/2014 |
| CN | 104147309 A | 11/2014 |
| EP | 0987027 A1 | 3/2000 |
| EP | 1495762 A1 | 1/2005 |
| EP | 1495764 A1 | 1/2005 |
| EP | 2489358 A1 | 8/2012 |

(Continued)

OTHER PUBLICATIONS

Naganuma et al. (2018) Gastroenterology vol. 154(4): 935-947. (Year: 2018).*
Balci et al. (2009) Eur. J. Dermatology 19(3): 238-42. (Year: 2009).*
Bastien et al. (1997) Arch. Dermatol. vol. 133, 1463-1465. (Year: 1997).*
Leyden et al. (1974) British Journal of Dermatol. 90: 525-530. (Year: 1974).*
Lin et al. (2007) Dermatology 214: 155-161. (Year: 2007).*
Hsieh et al. (2012) Journal of Dermatological Science, 67: 140-146. (Year: 2012).*
Lin et al. (2009) Journal of Dermatological Science 54: 168-174. (Year: 2009).*

(Continued)

*Primary Examiner* — Terry A McKelvey
*Assistant Examiner* — Russell G Fiebig
(74) *Attorney, Agent, or Firm* — Ice Miller LLP

(57) ABSTRACT

A pharmaceutical or cosmetic composition is provided. The composition includes an Indigo Naturalis or Indigo-producing plant extract, for inhibiting *Staphylococcus aureus*, including methicillin-resistant *Staphylococcus aureus*. A method of inhibiting *Staphylococcus aureus*, including methicillin-resistant *Staphylococcus aureus*, is also provided. The method includes contacting a cell with an effective amount of an Indigo Naturalis or Indigo-producing plant extract.

17 Claims, No Drawings

(56) References Cited

FOREIGN PATENT DOCUMENTS

| | | | |
|---|---|---|---|
| JP | H02264727 A | 10/1990 | |
| JP | 2002138047 A | 5/2002 | |
| JP | 2003002989 A | 1/2003 | |
| JP | 2006-241080 A | 9/2006 | |
| JP | 2007326855 A | 12/2007 | |
| JP | 2012520309 A | 9/2012 | |
| JP | 2014517021 | 7/2014 | |
| JP | 2015017044 A | 1/2015 | |
| KR | 2005-077310 A | 8/2005 | |
| KR | 2005077310 | 8/2005 | |
| KR | 2013-0071857 A | 7/2013 | |
| TW | 201436800 A | 10/2014 | |
| WO | 0061159 A1 | 10/2000 | |
| WO | 2005076757 A2 | 8/2005 | |
| WO | 2008062861 A1 | 5/2008 | |
| WO | 2012124743 A1 | 9/2012 | |
| WO | 2014118040 A1 | 8/2014 | |
| WO | 2014134394 A1 | 9/2014 | |

OTHER PUBLICATIONS

Miyoshi et al. (2012) Journal of Dermatological Science 65: 70-72. (Year: 2012).*
Ponnusamy et al. (2010) Scandinavian Journal of Infectious Diseases 42: 500-505 (Year: 2010).*
Raskin et al. (2004) Current Pharmaceutical Design, 10: 3419-3429. (Year: 2004).*
Revilla et al. (1998) J. Agric. Food Chem. 46: 4592-4597. (Year: 1998).*
Yarwood et al. (2000) FEMS Microbiology Letters 192:1-7 (Year: 2000).*
Int'l Search Report and Written Opinion dated Jun. 20, 2016 in Int'l Application No. PCT/EP2016/057761.
Int'l Search Report and Written Opinion dated Jun. 20, 2016 in Int'l Application No. PCT/EP2016/057763.
Int'l Search Report and Written Opinion dated Jun. 21, 2016 in Int'l Application No. PCT/EP2016/057769.
Han et al, "Genuine traditional Korean medicine, Naju Jjok (Chung-Dae Polygonum tinctorium) improves 2,4-dinitrofluorobenzene-induced atopic dermatitis-like lesional skin," Phytomedicine, vol. 24, pp. 453-460 (2014).
Han et al, "Tryptanthrin ameliorates atopic dermatitis through down-regulation of TSLP," Archives of Biochemistry and Biophysics, vol. 542, pp. 14-20 (2013).
Chiang, "An in Vitro Study of the Antimicrobial Effects of Indigo Naturalis Prepared from Strobilanthes Formosanus Moore", Molecules, vol. 18, No. 11, pp. 14381-14396 (2013).
Yang et al, "The Synergistic Activity of Antibodies Combined With Eight Traditional Chinese Medicines Against Two Different Strains of *Staphylococcus aureus*," Colloids and SurfacesB: Biointerfaces, vol. 41, pp. 79-81 (2005).
Shahni et al, "Antibacterial Properties of Leaf Extracts of *Strobilanthes cusia* (Nees) Kuntze, A Rare Ethno-Medicinal Plant of Manipur, India," International Journal of PharmTech Research, vol. 5, No. 3, pp. 1281-1285 (2013).
Ravichandran et al, "Phytochemical Screening and In-Vitro Antibacterial Activity of Leaf Extracts of Indigofera Tinctoria Linn," International Journal of Advances in Pharmaceutical Research, vol. 3, Issue 4, pp. 872-877 (2012).
Ponnusamy et al, "Indirubin Potentiates Ciprofloxacin Activity in the NorA Efflux Pump of *Staphylococcus aureus*," Scandinavian Journal of Infectious Diseases, vol. 42, pp. 500-505 (2010).
Thangadurai et al, "Indigoferabietone, A Novel Abietane Diterpenoid From Indigofera longeracemosa With Potential Antituberculous and Antibacterial Activity," Pharmazie, vol. 57, pp. 714-715 (2002).
Int'l Search Report dated Jun. 21, 2016 in Int'l Application No. PCT/EP2016/057775.
Tang et al, "Qingdai", Chinese Drugs of Plants Origin, vol. 103, pp. 805-806 (1992).
Lin et al, "Protective Effect of Indigo Naturalis Extract Against Oxidative Stress in Cultured Human Keratinocytes," Journal of Ethnopharmacology, vol. 139, Issue 3, pp. 893-896 (2012).
Liang et al, Successful Treatment of Pediatric Nail Psoriasis With Periodic Pustular Eruption Using Topical Indigo Naturalis Oil Extract, Pediatric Dermatology, vol. 30, No. 1, pp. 117-119, (2012).
Extended European Search Report dated Apr. 19, 2017 in EP Application No. 18211851.
Office Action dated Apr. 5, 2019 in U.S. Appl. No. 16/261,773 by Chantalat.
Wang et al., "Effects of indigo naturalis on colonic mucosal injuries and inflammation in rats with dextran sodium sulphate-induced ulcerative colitis" Experimental and Therapeutic Medicine, 14, pp. 1327-1336, 2017.
Zhang et al., "Improvement on Solvents of Extracting Indirubin from Qingdai," Journal of Guangxi Normal University: Natural Science Edition, vol. 24, No. 3, pp. 58-60 (2006).
Duan et al., "Optimal Extraction of Technology of Indigo Naturalis by Uniform Design," Modern Chinese Applied Pharmacy, vol. 29, No. 4, pp. 326-329 (2012).
Kim et al., "Indirubin, a purple 3,2-bisinodole, inhibited allergic contact dermatitis via regulating T helper (Th)-mediated immune system in DNCB-induced model", Journal of Ethnopharmacology, vol. 145, pp. 214-219, 2013.

* cited by examiner

ANTIBACTERIAL INDIGO NATURALIS OR INDIGO-PRODUCING PLANT EXTRACT AND USE THEREOF

CROSS-REFERENCE TO RELATED APPLICATION

This application is a Section 371 of International Application No. PCT/EP2016/057775, filed Apr. 8, 2016, which was published in the English language on Oct. 13, 2016, under International Publication No. WO 2016/162490 A1, and the disclosure of which is incorporated herein by reference.

TECHNICAL FIELD

The present invention relates to an antibacterial Indigo Naturalis or Indigo-producing plant extract and use thereof, particular for treating a skin disease or condition caused by *Staphylococcus aureus* (*S. aureus*) hypercolonization or infection.

BACKGROUND

Indigo Naturalis is a dark blue powder obtained from the leaves of indigo-bearing plants, such as *Baphicacanthus cusia*. Indigo Naturalis is a centuries-old Chinese herbal remedy used for antipyretic, anti-inflammatory, antiviral, antimicrobial, and detoxifying purposes.

It is always desirable to develop an antibacterial Indigo Naturalis extract which is useful for treating a skin disease or condition caused by *S. aureus* including methicillin-resistant *Staphylococcus aureus* (MRSA).

The pathologies or skin conditions that could be treated are: Superficial skin infections including impetigo, folliculitis, furuncles, carbuncles, superinfected skin diseases and hyper colonized skin conditions including atopic dermatitis and other conditions where the skin barrier is altered.

SUMMARY

The present invention relates to an Indigo Naturalis or Indigo-producing plant extract and pharmaceutical or cosmetic compositions comprising said Indigo Naturalis or Indigo-producing plant extract for inhibiting a bacterium mentioned in the present invention and for treating a skin disease caused by the bacterium.

In one aspect, the present invention provides an Indigo Naturalis or Indigo-producing plant extract for inhibiting a bacterium selected from the group consisting of *Bacillus subtilis*, *Staphylococcus aureus*, methicillin-resistant *Staphylococcus aureus*, *Staphylococcus epidermis*, *Streptococcus pneumoniae*, *Escherichia coli*, *Klebsiella pneumoniae*, and *Pseudomonas aeruginosa*. Preferably the bacterium is methicillin-resistant *Staphylococcus aureus*.

In some embodiments, the present invention provides an Indigo Naturalis or Indigo-producing plant extract for a use in the treatment of a skin disease caused by one or more of the aforesaid bacteria. In another aspect, the present invention provides a pharmaceutical or cosmetic composition comprising an Indigo Naturalis or Indigo-producing plant extract, for inhibiting a bacterium selected from the group consisting of *Bacillus subtilis*, *Staphylococcus aureus*, methicillin-resistant *Staphylococcus aureus*, *Staphylococcus epidermis*, *Streptococcus pneumoniae*, *Escherichia coli*, *Klebsiella pneumoniae*, and *Pseudomonas aeruginosa*. Preferably the bacterium is methicillin-resistant *Staphylococcus aureus*.

In a particular embodiment, the Indigo Naturalis or Indigo-producing plant extract comprises indirubin in an amount of at least 65% w/w of the extract, preferably 65-90% w/w of the extract.

In some embodiments, the present invention provides a pharmaceutical or cosmetic composition comprising an Indigo Naturalis or Indigo-producing plant extract, which is used for treating a skin disease caused by one or more of the bacteria.

In another aspect, the present invention provides a method of inhibiting a bacterium selected from the group consisting of *Bacillus subtilis*, *Staphylococcus aureus*, methicillin-resistant *Staphylococcus aureus*, *Staphylococcus epidermis*, *Streptococcus pneumoniae*, *Escherichia coli*, *Klebsiella pneumoniae*, and *Pseudomonas aeruginosa*, comprising contacting, including in vitro or in vivo, an effective amount of an Indigo Naturalis or Indigo-producing plant extract to a cell in need thereof.

In some embodiments, the present invention provides a method of the treatment of a skin disease caused by one or more bacteria selected from the group consisting of *Bacillus subtilis*, *Staphylococcus aureus*, methicillin-resistant *Staphylococcus aureus*, *Staphylococcus epidermis*, *Streptococcus pneumoniae*, *Escherichia coli*, *Klebsiella pneumoniae*, and *Pseudomonas aeruginosa*, comprising administering an effective amount of an Indigo Naturalis or Indigo-producing plant extract to a subject in need thereof.

In another aspect, the present invention provides use of an Indigo Naturalis or Indigo-producing plant in the preparation of a medicament for inhibiting a bacterium selected from the group consisting of *Bacillus subtilis*, *Staphylococcus aureus*, methicillin-resistant *Staphylococcus aureus*, *Staphylococcus epidermis*, *Streptococcus pneumoniae*, *Escherichia coli*, *Klebsiella pneumoniae*, and *Pseudomonas aeruginosa*.

In some embodiments, the composition is used for treating a skin disease caused by one or more of the bacteria.

In some embodiments, *Staphylococcus aureus* may be selected from the group consisting of community-acquired methicillin-resistant *Staphylococcus aureus*, *Streptococcus pyogenes*, group B streptococci, group C streptococci and group G streptococci were tested.

The Indigo Naturalis or Indigo-producing plant extract includes any extract obtained from an Indigo Naturalis or Indigo-producing or Indigo-bearing plant as starting material.

DETAILED DESCRIPTION

It is to be understood that, if any prior art publication is referred to herein, such reference does not constitute an admission that the publication forms a part of the common general knowledge in the art.

Indigo Naturalis, also known as Qingdai, is obtained from one or more plants including *Indigofera tinctoria* L., *Baphicacanthus cusia* (Nees) Bremek (syn. *Strobilanthes cusia* (Nees), *Persicaria tinctoria* (Aiton) Spach. (syn. *Polygonum tinctorium* Aiton, *P. tinctorium* Lour.), *Isatis tinctoria* L. (syn. *Isatis indigotica* Fort.) and *S. formosanus*, such as from the plant leaves or stems, and the leaves and/or stems, after harvest and collection, may be processed by, for example, fermentation. Qingdai is the current name for Indigo Naturalis. Indigo Naturalis is usually a dark-blue powder. It is obtained from Indigo-bearing or Indigo-producing plants with a NaOH or KOH aqueous solution and corresponds to a mixture of around 5-15% organic compounds including alkaloids among which indigo and indirubin are present, and 85-95% inorganic compounds such as calcium carbonate and calcium hydroxide.

An Indigo Naturalis or Indigo-producing plant extract, as used herein, refers to an extract from Indigo Naturalis or from the leaves and/or stems (or a part thereof) of one or more Indigo-bearing plant or Indigo-producing plant, where the extraction may be performed by using organic solvents and/or non-organic solvents, or a combination thereof. The extract may include enriched ingredient (having a higher w/w percentage than that existing in Indigo Naturalis) such as tryptanthrin, isatin, indirubin, indigo, or qingdainone. The extract may be a solid, liquid, or any form in-between (e.g., semi-solid).

In a particular embodiment, the Indigo Naturalis or Indigo-producing plant extract is enriched in indirubin, for example the extract may contain indirubin in an amount of at least 65% w/w of the extract, for example, 65%-90% w/w of the extract. The extract may further contain indigo in an amount of 0.1%45% w/w of the extract. The extract may also contain tryptanthrin and/or qingdainone each in an amount of 0.1-5% w/w.

One example of the Indigo Naturalis or Indigo-producing plant extract is an ethyl acetate extract (EA-extract), which may be prepared as Example 1 in the present invention. The content of each ingredient in the extract may vary. As an example, the extract may contain indirubin in an amount of at least 65% w/w of the extract, for example, 65%-90% w/w of the extract. The extract may further contain indigo in an amount of 0.5%-15% w/w of the extract. The extract may also contain tryptanthrin and/or qingdainone in an amount of 0.1-5% w/w, respectively.

A further example of Indigo Naturalis extract is an oil extract, particularly an olive oil extract. An oil extract can be prepared by the method disclosed in the U.S. Pat. No. 8,784,905. More specifically, the oil extract of Indigo Naturalis is an oil-extracted product of Indigo Natural's which is obtained by a process comprising extracting Indigo Naturalis powder with an oil under heating, optionally followed by a refining treatment by filtration. More preferably, in said process, the oil-extracted product is obtained after the refining treatment has a decreased indigo content. In said process, extracting Indigo Naturalis powder is more particularly conducted at an elevated temperature not higher than 155° C. and preferably conducted at a temperature ranging from 100° C. to 155° C. The oil used in said process is preferably selected from the group consisting of vegetable oils, animal oils, mineral oils, and combinations thereof. More preferably, the oil is a vegetable oil and can be selected from the group consisting of olive oil, cottonseed oil, sesame oil, sunflower seed oil, peanut oil, wheat germ oil, soybean oil, jojoba oil, evening primrose oil, coconut oil, palm oil, sweet almond oil, aloe oil, apricot kernel oil, avocado oil, borage oil, hemp seed oil, macadamia nut oil, rose hip oil, pecan oil, hazelnut oil, sasanqua oil, rice bran oil, shea butter, corn oil, *camellia* oil, grape seed oil, canola oil, castor oil, and combinations thereof. The content of each ingredient in the extract may vary. As an example, the extract may contain indirubin in an amount of at least 65% w/w of the total amount of extracted alkaloids, for example, 65%-90% w/w of the total amount of extracted alkaloids. The extract may further contain indigo in an amount of 0.1%45% w/w of the total amount of extracted alkaloids. The extract may also contain tryptanthrin and/or qingdainone each in an amount of 0.1-5% w/w of the total amount of extracted alkaloids.

Another example of Indigo Naturalis or Indigo-producing plant extract is an extract prepared by a process comprising the following steps:
a) an extraction step: extracting Indigo Naturalis or the leaves and/or stems of one or more Indigo-bearing plants or Indigo-producing plants, preferably selected from the group consisting of *Indigofera tinctoria* L., *Baphicacanthus cusia* (*Nees*) *Bremek* (syn. *Strobilanthes cusia* (*Nees*)), *Persicaria tinctoria* (Aiton) *Spach.* (syn. *Polygonum tinctorium* Aiton, *P. tinctorium* Lour.) and *Isatis tinctoria* L. (syn. *Isatis indigotica* Fort.) and/or *Strobilanthes Formosanus*, with a first polar solvent or moderately polar solvent to obtain a mixture of extraction;
b) a filtration step: filtering the mixture of extraction to obtain a filtrate;
c) a concentration step: concentrating the filtrate to obtain a crude extract;
d) a washing step: washing the crude extract with a non-polar solvent, and optionally a second polar solvent, to obtain a washing mixture; and
e) a filtration step: filtering the washing mixture to obtain a refined extract optionally after a drying step, for example, according to a conventional method for drying.

In a particular embodiment, a crude extract obtained from the concentration step c) is subjected to the following procedure for at least one cycle till obtaining a refined extract: the crude extract is washed by a solvent (step d)), and filtered (step (e)) to yield a refined extract, optionally followed by a drying step. According to a specific embodiment, the washing step d) and filtration step e) are performed by only one cycle to obtain the refined extract. When more than one cycle is applied, the same or different solvents for washing can be used. Further, the crude extract can be washed with a solvent under reflux, the mixture can be cooled to room temperature and then filtered to yield a refined extract, optionally followed by a drying step.

In a preferred embodiment, two cycles are performed. Particularly, the crude extract obtained by the concentration step c) is washed in a non-polar solvent, preferably hexane (step d) and filtered (step e), optionally followed by a drying step. The hexane extract is then washed by an organic polar solvent, preferably ethanol (step d) and then filtered (step e) to obtain a refined extract, optionally followed by a drying step.

Optionally, a micronization step is performed after step e), providing thereby a refined extract having a particle size between 25 and 35 μm, preferably of about 30 μm.

In another preferred embodiment, when the refined extract is micronized in the last step, 99% of the obtained particles are less or equal to 30 μm.

In a preferred embodiment, a refined extract may be prepared by a process comprising the following steps consisting of: a) (i) adding an extracting solvent, a polar or moderately polar solvent (such as an alcohol or ethyl acetate), to Indigo Naturalis powder to yield a mixture; (ii) heating and stirring the mixture for a period of time (e.g., 30 min, 1 hour, 2 hours); b) (iii) filtering the heated mixture while hot to remove insoluble by-products to yield a filtrate; c) (iv) concentrating the filtrate to yield a crude extract; d) (v) adding a washing solvent (for example, water a non-polar and/or a polar solvent or a mixture thereof) to the crude extract to yield a washing mixture; (vi) heating and stirring the washing mixture for a period of time (e.g., 30 min, 1 hour, 2 hours); e) (vii) filtering the washing mixture, for example at room temperature (e.g. 18-35° C.) to collect a refined extract; optionally (viii) repeating steps (v) to (vii) until the amount of indirubin (% w/w) in the refined extract is more than 55% (w/w), preferably more than 65% (w/w) as measured by HPLC method, and optionally (ix) drying the residue according to a conventional method (e.g., air-drying, lyophilization) to obtain a dried extract. The washing solvent in steps (v) and (viii) can be the same or different.

In a more preferred embodiment, a refined extract is prepared by a process comprising the steps of:
a) extracting Indigo Naturalis with ethanol at reflux between 2 and 8 hours,
b) filtering the mixture at a temperature not less than 65° C. to obtain a filtrate,
c) concentrating the filtrate, to obtain a crude extract, said crude extract is optionally filtered (with addition of water) in order to remove completely the solvent and the last components still present in the solvent and dried,
d) (i) washing the crude extract with hexane at a temperature not less than 50° C. between 15 and 60 min,
   (ii) filtering at room temperature the mixture obtained at step d) (i) to obtain a product, optionally rinsing it with ethanol and water
   (iii) washing the product obtained at step d) (ii) with ethanol at reflux, and
e) filtering at room temperature the washing mixture obtained at step d) and drying the resulting product at a temperature less than 80° C. to obtain an extract which is optionally micronized.

In another preferred embodiment, when the refined extract is micronized in the last step, the particle size is around 99% in the range 25 to 35 µm, preferably of about 30 µm.

As used herein, "about" or "around" will be understood by a person of ordinary skill in the art and will vary to some extent on the context in which it is used. If there are uses of the term which are not clear to persons of ordinary skill in the art given the context in which it is used, "about" or "around" will mean up to plus or minus 20%, preferably 10% of the particular term.

The term "refined extract", as used herein, refers to a solid, semi-solid or oily extract which contains less than 10% (w/w) of water and/or solvents used in the process for preparing the said refined extract. A refined extract is more preferably characterized by an increase amount of active ingredients, including alkaloids among which indigo, indirubin, tryptanthrin, and/or qingdainone are present, preferably enriched in indirubin, compared to Qingdai or Indigo Naturalis. More specifically, the refined extract according to the invention comprises at least 60%, or more preferably more than 65%, (w/w) of active ingredients, including indigo, indirubin, tryptanthrin, and/or qingdainone.

The term "crude extract", as used herein, refers to a solid, semi-solid or oily extract which contains less than 15% (w/w) (e.g., 5-15%, 5-10%) of water and/or solvents used in the process for preparing the refined extract. The crude extract is less enriched in indirubin, than the refined extract as compared to Qingdai or Indigo Naturalis. The crude extract is obtained by the concentration step c) according to the invention. The concentration step is more particularly carried out by sending the filtrate to a concentrator (for instance at reduced pressure), as to remove water and/or solvents used in the process and concentrating thereby the active ingredients present in the extract, including indigo, indirubin, tryptanthrin, and/or qingdainone.

"one cycle", as used herein, refers to the two steps of the washing step d) and filtration step e) which are performed sequentially once. "two cycles", as used herein, refers to the two steps of the washing step d) and filtration step e) which are performed sequentially twice.

According to a specific embodiment, the Indigo Naturalis or Indigo-producing plant extract according to the invention is an oil extract as defined above or an extract of Indigo-producing plant obtained by the process as above detailed comprising steps (a)-(e), optionally including one of the above described specific embodiments.

A skin disease caused by one or more aforesaid bacteria, used herein, refers to a condition or a disease caused by invasion of one or more of the bacteria to normal skin or broken skin from, for example, eczema/dermatitis or wounds.

An effective amount, as used herein, refers to a dose level of an Indigo Naturalis or Indigo-producing plant extract that yields a therapeutic benefit (for example, amelioration, alleviation or cure of the diseases, disorder or symptoms of a skin caused by one or more aforesaid bacteria) to a patient on average; or a dose level of an Indigo Naturalis or Indigo-producing plant extract that inhibits growth of a bacterium or killing a bacterium.

The present invention provides a composition comprising an Indigo Naturalis or Indigo-producing plant extract for inhibiting *Staphylococcus aureus*, including methicillin-resistant *Staphylococcus aureus*. The Indigo Naturalis or Indigo-producing plant extract may be used for treating a skin disease caused by one or more of the aforesaid bacteria, preferably for topically treating said skin disease. The Indigo Naturalis or Indigo-producing plant extract may be used directly without further formulation, or included in a pharmaceutical or cosmetic composition that comprises the extract.

The extract may comprise indirubin in an amount of at least 65% w/w of the extract, for example, 65%-90% w/w of the extract. It may further comprise indigo in an amount of 0.1%45% w/w of the extract, and in another further embodiment, the extract may also comprise indigo in an amount of 0.1%45% w/w of the extract and tryptanthrin and/or qingdainone each in an amount of 0.1-5% w/w of the extract.

The compositions, methods or uses of the invention may be used alone (i.e., in replacement of current treatments) or in combination with current treatments to improve their efficacy.

In an embodiment, Indigo Naturalis or Indigo-producing plant extract is used as the sole active ingredient (e.g. as a single therapy). According to this embodiment, the composition preferably comprises an Indigo Naturalis or Indigo-producing plant extract as the sole active ingredient.

In another embodiment, the Indigo Naturalis or Indigo-producing plant extract can be used in combination with at least one other therapy.

The pharmaceutical composition may be formulated into a suitable dosage form for topical or oral administration using technology well known to those skilled in the art. The pharmaceutical composition can additionally comprise a pharmaceutically acceptable carrier such as those widely employed in the art of drug-manufacturing. For instance, the pharmaceutically acceptable carrier may include one or more of the following agents: solvents such as olive oil, olive oil refined, cottonseed oil, sesame oil, sunflower seed oil, peanut oil, wheat germ oil, soybean oil, jojoba oil, evening primrose oil, coconut oil, palm oil, sweet almond oil, aloe oil, apricot kernel oil, avocado oil, borage oil, hemp seed oil, macadamia nut oil, rose hip oil, pecan oil, hazelnut oil, sasanqua oil, rice bran oil, shea butter, corn oil, *camellia* oil, grape seed oil, canola oil, castor oil, and combinations thereof, preferably olive oil refined, emulsifiers, suspending agents, decomposers, binding agents, excipients, stabilizing agents, chelating agents, diluents, gelling agents, thickening agent such as beeswax and/or petroleum jelly, preservatives, lubricants, absorption delaying agents, liposomes, antioxidants such as butylhydroxytoluene or butylhydroxyanisole and the like. A topical formulation suitable for the pharmaceutical composition may be an emulsion, a gel, an ointment, a cream, a patch, an embrocation, an aerosol, a spray, a lotion, a serum, a paste, a foam, or a drop. In some embodiments, the pharmaceutical composition is formulated into an external preparation by admixing the extract according to the present invention with a base such as those that are well known and commonly used in the art.

According to a specific embodiment, the compositions, methods or uses of the invention are suitable for a topical treatment of a skin disease caused by a bacterium.

In some embodiments, the dosage and the frequency of administration of the pharmaceutical composition according to the present invention may vary depending on the following factors: the severity of the disease to be treated, the route of administration, and the weight, age, physical condition and response of the subject to be treated. In further or additional embodiments, the amount of the extract is in the range of about 0.001 to about 1000 mg/kg body weight/day, for example, about 0.01 to about 500, 300, or 100 mg/kg body weight/day. In further or additional embodiments, administration can be performed daily or even several times per day, if necessary. By way of examples, the extract of the invention can be administered once, twice, three, four, five or six times a week or more, or once, twice, three or four times a day or more. Duration of the treatment may vary and depends on the severity of the disease. It may last for instance from one week to several months (such as from 2, 3, 4, 5, 6 or 7 weeks to 12, 18, 24, 30, or 36 weeks).

The present invention also provides a cosmetic composition comprising the extract. The composition may be present in a form adapted for topical application comprising a cosmetically or dermatologically acceptable carrier or medium. "Cosmetically or dermatologically acceptable" means media which are suitable for a use in which they come into contact with the skin or human skin appendages without posing a risk of toxicity, intolerance, instability, allergic reaction, etc. In the cosmetic composition, the extract may be previously solubilized in one or more cosmetically or dermatologically acceptable solvents, such as water, glycerol, ethanol, propylene glycol, butylene glycol, dipropylene glycol, ethoxylated or propoxylated diglycols, cyclic polyols, petroleum jelly, a vegetable oil or any mixture of these solvents.

The composition according to the invention may contain 0.001-10 mg, for example 0.01-1 mg of one or more active ingredients per 1 g composition.

The present invention also provides a method of inhibiting a bacterium selected from the group consisting of *Bacillus subtilis, Staphylococcus aureus,* methicillin-resistant *Staphylococcus aureus, Staphylococcus epidermis, Streptococcus pneumoniae, Escherichia coli, Klebsiella pneumoniae,* and *Pseudomonas aeruginosa,* by contacting an effective amount of an Indigo Naturalis or Indigo-producing plant extract or a compound selected from the group consisting of tryptanthrin, isatin, and a derivative thereof to a cell in need thereof. Further, the present invention provides a method of the treatment of a skin disease caused by one or more of the aforesaid bacteria by administering an effective amount of Indigo Naturalis or Indigo-producing plant or a compound selected from the group consisting of tryptan- thrin, isatin, and a derivative thereof to a subject in need thereof. The extract and compositions above can be used in the treatment or alleviation of a disease or condition. By treatment it is meant at least an alleviation of the symptoms associated with the pathological condition afflicting the subject, where alleviation is used in a broad sense to refer to at least a reduction in the magnitude of a parameter, e.g. symptom, associated with the pathological condition being treated. As such, treatment also includes situations where the pathological condition, or at least symptoms associated therewith, are completely inhibited, e.g., prevented from happening, or stopped, e.g., terminated, such that the host no longer suffers from the pathological condition, or at least the symptoms that characterize the pathological condition. As such, treatment includes both curing and managing a disease condition. Accordingly, the extract and compositions above can be used in the treatment or alleviation of a skin caused by one or more aforesaid bacteria.

The efficacy of the extract and compositions can be evaluated by in vivo models with respect to their activities in treating diseases or disorders, for example, clinically trails on humans.

The novel features of the application are set forth with particularity in the appended claims. A better understanding of the features and advantages of the present application will be obtained by reference to the following detailed description that sets forth illustrative embodiments, in which the principles of the application are utilized.

While embodiments of the present invention have been shown and described herein such embodiments are provided by way of example only. It should be understood that the above described embodiments may be combined if compatible and various alternatives to the embodiments of the invention described herein may be employed in practicing the invention. Those ordinary skilled in the art will appreciate that numerous variations, changes, and substitutions are possible without departing from the invention. It is intended that the following claims define the scope of aspects of the invention and that methods and structures within the scope of these claims and their equivalents be covered thereby.

It is to be understood that, if any prior art publication is referred to herein, such reference does not constitute an admission that the publication forms a part of the common general knowledge in the art. All documents, or portions of documents, cited in the invention including, without limitation, patents, patent applications, articles, books, manuals, and treatises are hereby expressly incorporated by reference in their entirety for any purpose.

The percentage herein is expressed by weight relative to the weight of the extract, unless otherwise specified.

Further aspects and advantages of the invention will be disclosed in the following illustrative experimental section.

EXAMPLES

1. Preparation Examples 1.1 Preparation of Indigo-Producing Plant (Example 1)

*S. formosanus* was harvested in Sansia, New Taipei City, Taiwan. The harvested leaves of *S. formosanus* were immersed in water for several days until the leaves were decomposed by microbial activities. After that, lime was added to the suspension to precipitate Indigo Naturalis.

1.2 Preparation of Ethyl Acetate (EA) Extracts of *S. formosanus* and Indigo Naturalis (Example 2)

The leaves of *S. formosanus* were dried in an oven (40° C.) for three days. Twenty-five g of the dried *S. formosanus* leaves were extracted with 300 mL of EA at 40° C. for one hour. Indigo Naturalis (25 g) was also extracted by the same procedure. The EA-extractable compounds of the two samples were then separated from the residue by centrifugation (12,000×g, 20 min) at 15° C. The supernatant was recovered and evaporated to dryness under reduced pressure and stored at −20° C. for bioassays.

1.3. Preparation of a Refined Indigo Naturalis Extract

Example 3

Qingdai as used in the following preparation is obtained from Delong Pharmaceutical (Indigo 2.62% and Indirubin 0.284% (HPLC method depicted in Example 7A) and tryptanthrin 0.0046%.

500 g of Qingdai were suspended in 10 L ethyl acetate. The mixture was stirred in reflux for two hours, and then filtered at 75° C. The filtrate was concentrated at reduced pressure to yield a dark solid. The crude extract was stirred in 250 mL hexane and heated to reflux for one hour. After cooling to room temperature, the suspension was filtered to give a dark residue.

0.50 g of the dark residue were refluxed in 25 mL hexane again for one hour, and cooled to room temperature, followed by filtration to give a refined extract as a dark red solid 452 mg. HPLC: 62.9% indirubin, 12.9% indigo, and 0.53% tryptanthrin.

Example 4

500 g of Qingdai as used in Example 1 were suspended in 10 L alcohol (ethanol). The mixture was stirred in reflux for two hours, and then filtered at 75° C. The filtrate was concentrated at reduced pressure to yield a dark solid, which was stirred in 260 mL hexane and heated to reflux for one hour. Upon cooling to room temperature, the suspension was filtered to give a dark residue.

0.80 g of the dark residue were refluxed in 24 mL alcohol (ethanol) for an additional hour, and then cooled to room temperature, followed by filtration to give a refined extract as a dark red solid (538 mg). HPLC: 83.6% indirubin, 6.35% indigo, and 0.75% tryptanthrin.

Example 5

500 g of Qingdai as used in Example 1 were suspended in 10 L ethyl acetate. The mixture was stirred in reflux for two hours, and then filtered while hot. The filtrate was concentrated at reduced pressure to yield a dark solid. The crude extract was stirred in 250 mL hexane and heated to reflux for one hour. After cooling to room temperature, the suspension was filtered to give a dark residue.

0.75 g of the dark residue were refluxed in 22.5 mL ethanol for one hour, and cooled to room temperature, followed by filtration to give a refined extract as a dark red solid (538 mg). HPLC: 77.9% indirubin, 15.9% indigo, and 0.56% tryptanthrin.

Example 6

500 g of Qingdai as used in Example 1 were suspended in 2.1 L DMF. The mixture was stirred at 50° C. for 40 minutes. Upon cooling to 20° C., the suspension was filtered. The filtrate was concentrated at reduced pressure to yield a dark solid, which was stirred in 130 mL hexane and heated to reflux for one hour. Upon cooling to 20° C., the suspension was filtered to give a dark residue.

1.56 g of the dark residue was washed with 46.8 ml ethanol, and heated to reflux for one hour, and then cooled to 20° C., followed by filtered to yield a refined extract (766 mg). HPLC: 66.3%, indirubin, 9.76% indigo.

Example 7

500 g of Qingdai as used in Example 1 were suspended in 3 L DMF. The mixture was stirred at 30° C. for 1 hour, and then filtered. The filtrate was concentrated at reduced pressure to yield a dark solid, which was stirred in 230 mL hexane and heated to reflux for one hour. Upon cooling to 20° C., the suspension was filtered to give a dark residue. 1.96 g of the dark residue was washed with 59 mL 85% ethanol (85% aq. alcohol), and heated to reflux for one hour followed by filtration while hot to yield a refined extract (1.02 g). HPLC: 69.4% indirubin, 18.7% indigo, and 0.62% tryptanthrin.

Example 8

100 g of Qingdai was extracted with 2 L of ethanol 92% (92% aqueous ethanol) for 2 hours under reflux conditions. Upon completion, the mixture was filtered while hot on AF6 filter (Buchner) to obtain a dark blue-red solution as a filtrate. This filtrate was reduced under vacuum to dryness to give 2.4 g of dry residue. This residue was washed with 120 mL of hexane for 1 h under reflux. Upon completion, the mixture was cooled to room temperature for 2 h then filtered under vacuum to yield 312.9 mg of a dark red refined extract.

280 mg of this refined extract were washed with 15 mL of ethanol 92% (92% aqueous ethanol) for 1 h under reflux. Upon completion the solution was cooled to room temperature, and then filtered to yield 159 mg of a dark red/burgundy refined extract after drying in oven (80° C.) for 1 h30. (0.18%); HPLC: 82.31% indirubin, 8.99% indigo, and 0.81% tryptanthrin.

Example 9

Micronization Step

The micronization step of refined Indigo Naturalis or Indigo-producing plant extract obtained in the previous examples is performed with the following equipment:

Micronizer: spiral jet Mill Diameter 200
    Feeder: this equipment is used for the dosage of powder to feed the micronizer. The dosage is made thanks to two screws. This system allows a regularity of the flow.

Micronization consists to project grains of powder with jet of air. The contact of grains permits their explosion.

Following parameters of micronization are recorded during the micronization:

Ring pressure: 6 bar
Injector pressure: 3 bar
The flow of powder feed: 25 kg/h

The micronizer allows a cylindrical enclosure—holes around the enclosure for the injection of air.

Powder is introduced in the micronizer; grains are propelled thanks to jet of air. When grains have the good size, they are concentrated in the center of the micronizer and they are breathed. To avoid any contamination by foreign particles or broken pieces of the equipment, an additional sieving (sieve: 700 μm) is performed.

The step is done manually after the micronization and before the packaging.

A granulometric analysis of the homogeneous product obtained was carried out according to the particular size distribution (PSD) method [Analytical specifications: D99≤30 μm].

2. Antimicrobial Activities of Indigo Naturalis Extract (1) Experimental Section Chemicals and Microbial Strains The chemicals used were of analytical grade and were purchased from BD Diagnostics (Sparks, Md., USA), Sigma-Aldrich (Saint Louis, Mo., USA), Merck (Darmstadt, Germany), and Roth (Karlsruhe, Germany). The antibacterial activities were tested against a wide range of bacteria including human pathogens such as *K. pneumoniae* ATCC 13883, *P. aeruginosa* ATCC 27853, *S. aureus* ATCC 6538, methicillin-resistant *S. aureus* (MRSA) ATCC 43300, and *Streptococcus pneumoniae* ATCC 33400 (Table 1). Tested bacterial strains were purchased from the American Type Culture Collection (ATCC; Manassas, Va., USA). The media used to cultivate these strains were prepared according to the recommended media list on the ATCC website (http://www.atcc.org).

Agar Diffusion Assay

To obtain fresh pre-cultures, the tested strains were first cultivated in a 60 ml medium in 250 ml Erlenmeyer flasks. The media and incubation temperature for the different bacterial strains are summarized in Table 1. Incubation was performed under aerobic conditions with shaking (180 rpm) and the growth of tested strains was determined by measuring the optical density (OD) at 600 nm. Cultures in the exponential growth phase ($OD_{600\ nm}$ reached 0.5~0.8; with an optical path of 1 cm) were diluted to $OD_{600\ nm}=0.1$, and immediately used for the following antimicrobial assays. The antimicrobial activities of EA extracts were tested by an agar diffusion assay described by Finn [Finn, R. K. Theory of Agar Diffusion Methods for Bioassay. *Anal Chem.* 1959, 31, 975-977]. The discs (6 mm diameter) containing bioactive compounds (10, 25, 50, or 100 μg per disc) were placed onto agar plates seeded with tested strains. Antimicrobial activities of bioactive compounds were tested in triplicate. The diameters of the inhibition zones (diameter of inhibition zone minus diameter of disc) were measured in mm after incubation at optimal temperature for 24 hours (see Table 1). For internal controls, authentic antibiotics (kanamycin, penicillin, and tetracycline for the test bacterial strains) were used.

Statistical Analysis

All experiments were repeated at least three times. Data were expressed as the mean±standard deviation.

(2) Antimicrobial Activities of Indigo Naturalis EA-Extract (Example 2)

In this study, agar diffusion assay was utilized to assess the antimicrobial effect of the Indigo Naturalis EA-extract (example 2 in the range between 0~4 mg per disc) because: (1) some tested microorganisms were unable to grow evenly in liquid media; (2) the color of Indigo Naturalis extract was dark-blue. These conditions made microtiter plate assay unsuitable for this study.

Five strains of Gram-positive, three strains of Gram-negative bacteria were used in the antimicrobial assay (Table 1). Among them, *S. aureus* ATCC 6538, MRSA ATCC 43300, *S. pneumoniae* ATCC 33400, *K. pneumoniae* ATCC 13883, and *P. aeruginosa* ATCC 27853 are pathogens in humans. In addition, *S. epidermis* ATCC 12228 is an opportunistic pathogen on skin.

TABLE 1

Microbial strains assayed for antimicrobial effects.

| Microbial strains | Growth temperature (° C.) | Media used for cultivation |
|---|---|---|
| Gram-positive bacteria | | |
| *Bacillus subtilis* ATCC 21778 | 30 | ATCC medium 3 |
| *Staphylococcus aureus* ATCC 6538 | 37 | ATCC medium 18 |
| methicillin-resistant*Staphylococcus aureus* (MRSA) ATCC 43300 | 37 | ATCC medium 18 |
| *Staphylococcus epidermis* ATCC 12228 | 37 | ATCC medium 3 |
| *Streptococcus pneumoniae* ATCC 33400 | 37 | ATCC medium 260 |
| Gram-negative bacteria | | |
| *Escherichia coli* ATCC 23815 | 37 | ATCC medium 3 |
| *Klebsiella pneumoniae* ATCC 13883 | 37 | ATCC medium 3 |
| *Pseudomonas aeruginosa* ATCC 27853 | 37 | ATCC medium 18 |

Table 2 shows the growth inhibitory activities of the Indigo Naturalis EA-extract (example 2) against tested bacteria. Results revealed that Indigo Naturalis EA-extract had significant inhibitory effects against *S. aureus*, *S. epidermis* and MRSA. Nevertheless, there was no inhibitory effect found in other Gram-positive and Gram-negative species in the presence of Indigo Naturalis EA-extract (<4 mg per disc). Moreover, the inhibitory activities of Indigo Naturalis EA-extract against the above three *Staphylococcus* strains varied in a dose-dependent manner (Table 2).

TABLE 2

The antimicrobial effects of Indigo Naturalis EA-extract on tested microorganisms.

| | Quantity of Indigo Naturalis EA-extract per disc (mg) | | | | |
|---|---|---|---|---|---|
| Test Strains | 0 mg | 1 mg | 2 mg | 3 mg | 4 mg |
| Gram-positivebacteria | | | | | |
| *B. subtilis* | 0 ± 0* | 0 ± 0 | 0 ± 0 | 0 ± 0 | 0 ± 0 |
| *S. aureus* | 0 ± 0 | 138 ± 18 | 157 ± 23 | 174 ± 17 | 188 ± 24 |
| MRSA | 0 ± 0 | 167 ± 13 | 198 ± 18 | 209 ± 25 | 225 ± 38 |
| *S. epidermis* | 0 ± 0 | 77 ± 8 | 86 ± 5 | 95 ± 13 | 108 ± 24 |
| *S. pneumoniae* | 0 ± 0 | 0 ± 0 | 0 ± 0 | 0 ± 0 | 0 ± 0 |
| Gram-negativebacteria | | | | | |
| *E. coli* | 0 ± 0 | 0 ± 0 | 0 ± 0 | 0 ± 0 | 0 ± 0 |
| *K. pneumoniae* | 0 ± 0 | 0 ± 0 | 0 ± 0 | 0 ± 0 | 0 ± 0 |
| *P. aeruginosa* | 0 ± 0 | 0 ± 0 | 0 ± 0 | 0 ± 0 | 0 ± 0 |

*The diameters of the inhibition zones (diameter of inhibition zone minus diameter of disc) were measured in mm after incubation at optimal temperature of individual test strains (see Table 1) for 24 hours. Data are the means of triplicates ± standard deviation of a representative experiment.

The results of the data indicate that Indigo Naturalis EA-extract can significantly inhibit *S. aureus*, MRSA and *S. epidermis*.

(3) Antimicrobial Activities of Indigo Naturalis Extract on Several *S. aureus* Strains Several staphylococci, including community-acquired methicillin-resistant *Staphylococcus aureus*, *Streptococcus pyogenes*, group B streptococci, group C streptococci and group G streptococci were tested. All isolates were obtained from cutaneous infections in outpatients. MICs of antibiotics were determined by the broth microdilution technique. Activity of Indigo Naturalis extract was tested by a method derived from protocol NFT 72-150 (without interfering substance) The medium used was unbuffered 0.9% saline, pH adjusted to pH 4 with HCl. MBC of Indigo Naturalis extract was defined as the lowest concentration of the compound that lead to a 5 log or greater drop from the starting bacterial concentration after 5 minutes of contact at 20° C. in 0.9% saline pH 4 (99.999% killing of the initial inoculum).

The invention claimed is:

1. A method of treating a skin disease comprising topically applying an effective amount an Indigo Naturalis extract to a subject in need thereof, wherein the Indigo Naturalis extract comprises relative to the total weight of the extract:
   65% to 90% (w/w) indirubin,
   0.1 to 15% (w/w) indigo; and
   0.01 to 5% (w/w) trytanthrin, and
wherein the skin disease is caused by one or more of the bacteria selected from the group consisting of *Baccillus subtilis, Staphylococcus aureus, methicillin-reistant Staphylococcus aureus, Staphylococcus epidermis, Streptococcus pneumonia, Escherichia coli, Klebsiella pneumonia,* and *Pseudomonas aeruginosa.*

2. The method according to claim 1, wherein the Indigo Naturalis extract is comprised in a pharmaceutical or cosmetic composition.

3. The method according to claim 1, wherein the Indigo Naturalis extract is obtained by the process comprising the steps of:
   a) extracting Indigo Naturalis with ethanol at reflux between 2 and 8 hours,
   b) filtering the mixture at a temperature not less than 65° C. to obtain a filtrate,
   c) concentrating the filtrate, to obtain a crude extract, said crude extract is optionally filtered (with addition of water) in order to remove completely the solvent and the last components still present in the solvent and dried,
   d) (i) washing the crude extract with hexane at a temperature not less than 50° C. between 15 and 60 min,
      (ii) filtering at room temperature the mixture obtained at step d) (i) to obtain a product, optionally rinsing it with ethanol and water,
      (iii) washing the product obtained at step d) (ii) with ethanol at reflux, and then
   e) filtering at room temperature the washing mixture obtained at step d) and drying the resulting product at a temperature less than 80° C. to obtain an extract which is optionally micronized.

4. The method of claim 3, wherein the skin disease is selected from the group consisting of superficial skin infection, superinfected skin disease and hyper colonized skin condition.

5. The method of claim 4, wherein the superficial skin infection is selected from the group consisting of impetigo, folliculitis, furuncles, and carbuncles, and the hyper colonized skin condition is atopic dermatitis.

6. The method of claim 3, wherein the extract is further micronized and comprises particles having a particle size of less than or equal to 30 μm in 99% of the particles.

7. The method of claim 1, wherein the extract further comprises 0.1-5% (w/w) qingdainone relative to the total weight of the extract.

8. The method according to claim 1, wherein the Indigo Naturalis or Indigo-producing plant extract is an oil extract.

9. The method of claim 1, wherein the extract is prepared by a process comprising:
   a) extracting Indigo Naturalis or leaves and/or stems of one or more plants selected from the group consisting of *Indigofera tinctoria* L., *Baphicacanthus cusia* (*Nees*) *Bremek* (syn. *Strobilanthes cusia* (*Nees*)), *Persicaria tinctoria* (*Aiton*) *Spach.* (syn. *Polygonum tinctorium Aiton, P. tinctorium Lour.*) and *Isatis tinctoria* L. (syn. *Isatis indigotica Fort.*) and/or *Strobilanthes Formosanus*, with a solvent to obtain a mixture of extraction, wherein the solvent is selected from the group consisting of dimethylformamide, ethyl acetate, ethanol, water, and a combination thereof,
   b) filtering the mixture of extraction to obtain a filtrate,
   c) concentrating the filtrate to obtain a crude extract,
   d) mixing the crude extract with hexane to obtain a first washing mixture,
   e) filtering the first washing mixture to obtain a first extract product,
   f) washing the first extract product with a washing method comprising:
      i. mixing the first extract product and a solvent selected from the group consisting of hexane, ethanol and an aqueous solution of ethanol to obtain a second washing mixture, and
      ii. filtering the second washing mixture at room temperature to obtain the extract product.

10. The method of claim 1, wherein the extract is prepared by a process comprising:
    a) extracting Indigo Naturalis or leaves and/or stems of one or more plants selected from the group consisting of *Indigofera tinctoria* L., *Baphicacanthus cusia* (*Nees*) *Bremek* (syn. *Strobilanthes cusia* (*Nees*)), *Persicaria tinctoria* (*Aiton*) *Spach.* (syn. *Polygonum tinctorium Aiton, P. tinctorium Lour.*) and *Isatis tinctoria* L. (syn. *Isatis indigotica Fort.*) and/or *Strobilanthes Formosanus*, with a solvent to obtain a mixture of extraction, wherein the solvent is selected from the group consisting of dimethylformamide, ethyl acetate, ethanol, water, and a combination thereof,
    b) filtering the mixture of extraction to obtain a filtrate,
    c) concentrating the filtrate to obtain a crude extract,
    d) mixing the crude extract with hexane to obtain a first washing mixture,
    e) filtering the first washing mixture to obtain a first extract product,
    f) washing the first extract product with a washing method comprising:
       i. mixing the first extract product and a solvent selected from the group consisting of hexane, ethanol and an aqueous solution of ethanol to obtain a second washing mixture,
       ii. filtering the second washing mixture at room temperature to obtain a second extract product, and
       iii. drying the second extract product at a temperature of less than 80° C. to obtain a dried extract product,
    g) optionally washing the dried extract product with the washing method of f) one or more times to obtain the extract.

11. The method of claim 10, wherein the extract is further micronized and comprises particles having a particle size of less than or equal to 30 μm in 99% of the particles.

12. The method of claim 1, wherein the extract further comprises 0.1-5% (w/w) qingdainone relative to the total weight of the extract.

13. The method of claim 1, wherein the skin disease is selected from the group consisting of superficial skin infection, superinfected skin disease and hyper colonized skin condition.

14. The method of claim 13, wherein the superficial skin infection is selected from the group consisting of impetigo, folliculitis, furuncles, and carbuncles, and the hyper colonized skin condition is atopic dermatitis.

15. A method of inhibiting *Staphylococcus aureus* (*S. aureus*) comprising administering an effective amount of an Indigo Naturalis extract to a cell in need thereof, wherein the Indigo Naturalis extract comprises relative to the total weight of the extract:
   65% to 90% (w/w) indirubin,
   0.1 to 15% (w/w) indigo; and
   0.01 to 5% (w/w) trytanthrin.

16. The method according to claim 15, wherein the Indigo Naturalis extract is an oil extract.

17. The method according to claim 15, wherein the Indigo Naturalis extract is obtained by the process comprising the steps of:

a) extracting Indigo Naturalis with ethanol at reflux between 2 and 8 hours, b) filtering the mixture at a temperature not less than 65° C. to obtain a filtrate, c) concentrating the filtrate, to obtain a crude extract, said crude extract is optionally filtered (with addition of water) in order to remove completely the solvent and the last components still present in the solvent and dried, d) (i) washing the crude extract with hexane at a temperature not less than 50° C. between 15 and 60 min,
   (ii) filtering at room temperature the mixture obtained at step d) (i) to obtain a product, optionally rinsing it with ethanol and water,
   (iii) washing the product obtained at step d) (ii) with ethanol at reflux, and then e) filtering at room temperature the washing mixture obtained at step d) and drying the resulting product at a temperature less than 80° C. to obtain an extract which is optionally micronized.

* * * * *